US012613176B2

(12) United States Patent
Akishika et al.

(10) Patent No.: US 12,613,176 B2
(45) Date of Patent: Apr. 28, 2026

(54) METHOD FOR EVALUATING THERMOPLASTICITY OF COAL OR CAKING ADDITIVE

(71) Applicant: JFE STEEL CORPORATION, Tokyo (JP)

(72) Inventors: Issui Akishika, Tokyo (JP); Yusuke Dohi, Tokyo (JP); Daisuke Igawa, Tokyo (JP)

(73) Assignee: JFE STEEL CORPORATION, Tokyo (JP)

(*) Notice: Subject to any disclaimer, the term of this patent is extended or adjusted under 35 U.S.C. 154(b) by 480 days.

(21) Appl. No.: 18/020,555

(22) PCT Filed: Aug. 5, 2021

(86) PCT No.: PCT/JP2021/029202
§ 371 (c)(1),
(2) Date: Feb. 9, 2023

(87) PCT Pub. No.: WO2022/039045
PCT Pub. Date: Feb. 24, 2022

(65) Prior Publication Data
US 2023/0296486 A1 Sep. 21, 2023

(30) Foreign Application Priority Data
Aug. 17, 2020 (JP) ................................. 2020-137312

(51) Int. Cl.
*G01N 11/14* (2006.01)
*G01N 3/54* (2006.01)
*G01N 33/22* (2006.01)

(52) U.S. Cl.
CPC ............... *G01N 11/14* (2013.01); *G01N 3/54* (2013.01); *G01N 33/222* (2013.01)

(58) Field of Classification Search
CPC ......... G01N 11/14; G01N 3/54; G01N 33/222
See application file for complete search history.

(56) References Cited

U.S. PATENT DOCUMENTS

| | | | |
|---|---|---|---|
| 12,061,140 B2 | 8/2024 | Akishika et al. | |
| 2014/0144071 A1 | 5/2014 | Dohi et al. | |

(Continued)

FOREIGN PATENT DOCUMENTS

| | | |
|---|---|---|
| CN | 104145181 A | 11/2014 |
| CN | 105122055 A | 12/2015 |

(Continued)

OTHER PUBLICATIONS

Oct. 27, 2023 Extended European Search Report issued in European Patent Application No. 21858192.4.

(Continued)

*Primary Examiner* — Lam S Nguyen
(74) *Attorney, Agent, or Firm* — Oliff PLC

(57) ABSTRACT

A method for evaluating the thermoplasticity of a coal or a caking additive with an apparatus including a container for coal and a stirrer located in the container. The method includes estimating a permeation distance of the coal or caking additive from a value indicating a shape of semicoke formed by rotating the stirrer while heating the coal or caking additive and from a correlation between the value indicating the shape of the semicoke and the permeation distance of the coal or caking additive.

4 Claims, 3 Drawing Sheets

(56)        References Cited

U.S. PATENT DOCUMENTS

| | | | | |
|---|---|---|---|---|
| 2017/0137716 A1* | 5/2017 | Dohi | .......................... | C10L 5/04 |
| 2023/0296486 A1 | 9/2023 | Akishika et al. | | |

FOREIGN PATENT DOCUMENTS

| | | | |
|---|---|---|---|
| CN | 106232776 | A | 12/2016 |
| CN | 110887763 | A | 3/2020 |
| EP | 2821774 | A1 | 1/2015 |
| EP | 2985602 | A1 | 2/2016 |
| EP | 3150687 | A1 | 4/2017 |
| JP | H01-233344 | A | 9/1989 |
| JP | 2001123179 | A | 5/2001 |
| JP | 2004-315664 | A | 11/2004 |
| JP | 2010-190761 | A | 9/2010 |
| JP | 5062353 | B2 | 10/2012 |
| JP | 6565642 | B2 * | 8/2019 |
| RU | 2562491 | C2 | 9/2015 |
| TW | 201217768 | A | 5/2012 |
| WO | 2015/146122 | A1 | 10/2015 |

OTHER PUBLICATIONS

Oct. 23, 2023 Office Action issued in Australian Patent Application No. 2021329613.

Sep. 21, 2021 International Search Report issued in International Patent Application No. PCT/JP2021/029202.

Mar. 21, 2022 Office Action issued in Taiwanese Patent Application No. 110129872.

Aug. 8, 2023 Written Decision on Registration issued in Russian Patent Application No. 2023102924/05.

Mar. 3, 2025 Office Action issued in U.S. Appl. No. 18/020,461.

May 17, 2024 Office Action issued in Canadian Patent Application No. 3,182,598.

Jun. 17, 2025 Office Action issued in Chinese Patent Application No. 202180056619.2.

Jun. 27, 2025 Office Action issued in European Patent Application No. 21 858 192.4.

Zhuang Yang et al., "Research Progress in caking property of coal". Energy Chemical Industry. Apr. 2017. vol. 38, No. 2. pp. 46-49.

\* cited by examiner

METHOD FOR EVALUATING THERMOPLASTICITY OF COAL OR CAKING ADDITIVE

TECHNICAL FIELD

This application relates to a method for evaluating the thermoplasticity of a coal or a caking additive used as a raw material for metallurgical coke.

BACKGROUND

Metallurgical coke used as a blast furnace raw material to produce pig iron in a blast furnace preferably has high strength. Low-strength coke used as a blast furnace raw material degrades in a blast furnace, and the powdered coke reduces the gas permeability in the blast furnace. Thus, pig iron cannot be stably produced. To produce high-strength coke or not to reduce the strength of coke, therefore, there is a need for a technique for examining a coal or a caking additive as a raw material for metallurgical coke.

Coke is produced in a coke oven by carbonizing a coal blend containing various coals for coke production pulverized to adjust the grain size. A coal or a caking additive for coke production is thermally plasticized by carbonization in the temperature range of approximately 300° C. to 550° C. and simultaneously foams and swells due to the generation of volatile matter. Thus, grains adhere to each other and form massive semicoke. The semicoke then contracts and is densified while being heated to approximately 1000° C. and forms hard coke (coke cake). Thus, the adhesiveness of the thermoplastic coal or caking additive has a great influence on the coke strength, grain size, and other properties after carbonization.

To examine the thermoplastic behavior of a coal or a caking additive in a coke oven, the thermoplasticity of the coal or caking additive should be measured under a condition simulating the environment around the coal or caking additive thermally plasticized in the coke oven. A coal or a caking additive thermally plasticized in a coke oven and the surrounding environment are described in detail below.

In a coke oven, coal is thermally plasticized while being restrained by an adjacent layer. The term "coal", as used herein, includes a mixture of coal and a caking additive. Coal, which has low thermal conductivity, is not uniformly heated in a coke oven and has different states, that is, a coke layer, a thermoplastic layer, and a coal layer from the furnace wall side, which is a heating surface. A coke oven itself expands somewhat but deforms little during carbonization, and thermoplastic coal is restrained by the adjacent coke and coal layers. Furthermore, there are a large number of defect structures around thermoplastic coal, such as voids between coal grains in the coal layer, voids between grains of the thermoplastic coal, coarse pores formed by volatilization of pyrolysis gas, and cracks formed in the adjacent coke layer. In particular, cracks formed in the coke layer are considered to have a width of hundreds of microns to several millimeters, which are larger than voids or pores between coal grains with a size of tens to hundreds of microns. It is thought that not only pyrolysis gas and a liquid material, which are by-products generated from coal, but also thermoplastic coal itself permeates into such a coarse defect in the coke layer. It is also expected that different brands of coal have different shear rates on thermoplastic coal during permeation.

Patent Literature 1 discloses a method for evaluating the thermoplasticity of a coal or a caking additive. More specifically, a sample is prepared by filling a container with a coal or a caking additive. A material with a through-hole in the top and bottom surfaces is put on the sample. The sample is heated under a constant load or while the sample and the material with a through-hole in the top and bottom surfaces maintain a constant volume. The permeation distance of a molten sample that has permeated into the through-hole of the material is measured. A method for evaluating the thermoplasticity of a coal or a caking additive using the measured value is also disclosed.

CITATION LIST

Patent Literature

PTL 1: Japanese Patent No. 5062353

SUMMARY

Technical Problem

However, the method for measuring the permeation distance disclosed in Patent Literature 1 is a method for measuring the permeation distance of molten coal or a molten caking additive in a material with a through-hole between the top and bottom surfaces while heating the coal or caking additive under load or while heating the coal or caking additive in a fixed volume. This requires special equipment, which causes a problem that the measurement cannot be started easily. In view of such situations, it is an object of the disclosed embodiments to provide a method for evaluating the thermoplasticity of coal that can easily estimate the permeation distance of a coal or a caking additive without special equipment.

Solution to Problem

Means for solving these problems are described below.

(1) A method for evaluating the thermoplasticity of a coal or a caking additive with an apparatus including a container for the coal or caking additive and a stirrer located in the container, including: estimating a permeation distance of the coal or caking additive from a value indicating a shape of semicoke formed by rotating the stirrer while heating the coal or caking additive and from a correlation between the value indicating the shape of the semicoke and the permeation distance of the coal or caking additive.

(2) The method for evaluating the thermoplasticity of a coal or a caking additive according to (1), wherein the value indicating the shape of the semicoke is at least one of a height, b, of the semicoke on an inner wall of the container, a height, a, of the semicoke adhering to the stirrer, a difference, a–b, between the height, a, and the height, b, and a degree of entanglement, (a–b)/a, represented by the height, a, and the height, b.

(3) The method for evaluating the thermoplasticity of a coal or a caking additive according to (1) or (2), wherein the apparatus is a Gieseler plastometer, and the coal or caking additive is heated to a temperature equal to or higher than a re-solidification temperature of the coal or caking additive.

Advantageous Effects

A method for evaluating the thermoplasticity of a coal or a caking additive according to the disclosed embodiments is performed with a Gieseler plastometer, which is widely used in facilities in which coal is used to produce coke. The permeation distance can be estimated from a value indicating the shape of semicoke after the measurement of Gieseler fluidity. Thus, the thermoplasticity of the coal or caking additive can be easily evaluated without special equipment.

DETAILED DESCRIPTION

The disclosed embodiments include a method for evaluating the thermoplasticity of a coal or a caking additive using as a measure a value indicating the shape of semicoke formed from the coal or caking additive heated with an apparatus including a container for the coal or caking additive and a stirrer located in the container. The inventors completed the disclosed embodiments by finding that each of the height, a, of semicoke adhering to a stirrer after measurement of Gieseler fluidity, the height, b, of the semicoke on the inner wall of the container, the difference between the height, a, of the semicoke adhering to the stirrer and the height, b, on the inner wall of the container, and the degree of entanglement, (a–b)/a, has a correlation with the permeation distance of coal. The disclosed embodiments are further described below.

Figure 1:
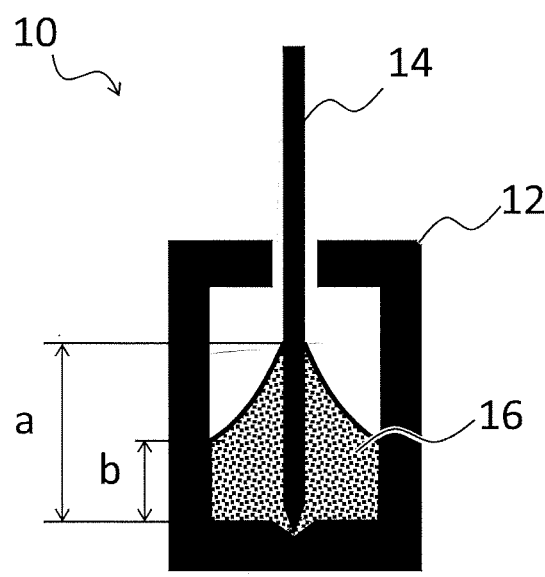
FIG. 1 is a vertical cross-sectional view of a Gieseler plastometer 10 that can be used in a method for evaluating the thermoplasticity of a coal or a caking additive according to the present embodiment.

FIG. 1 is a vertical cross-sectional view of an example of a Gieseler plastometer 10 used in a method for evaluating the thermoplasticity of a coal or a caking additive according to the present embodiment. The Gieseler plastometer 10 includes a container 12 for a coal or a caking additive to be examined and a stirrer 14 located in the container 12. The Gieseler plastometer 10 further includes a drive unit (not shown), which rotates the stirrer 14. When the container 12 containing a coal or a caking additive is heated while the stirrer 14 is rotated, the heated coal or caking additive has a thermoplastic state. The coal or caking additive deforms as a viscoelastic body and becomes entangled with the rotating stirrer 14. Force to maintain the shape acts on the coal or caking additive, and force to resist the rotation acts on the stirrer 14.

In a Gieseler plastometer method, the rotational speed of the stirrer 14 is measured while a predetermined torque is applied to the stirrer 14, and the maximum rotational speed during heating is determined as a Gieseler maximum fluidity MF (ddpm). The measured value may be represented by the common logarithm log of the Gieseler maximum fluidity expressed in log MF. The coal heating conditions and the conditions for measuring the dimensions of the container 12 or the like in the Gieseler plastometer method are specified in JIS M 8801 as described below.

(1) A stirrer having a shaft with a diameter of 4.0 mm and four horizontal bars (1.6 mm in diameter, 6.4 mm in length, not shown in FIG. 1) perpendicular to the shaft is placed in a container with a depth of 35.0 mm and an inner diameter of 21.4 mm.

(2) The container is filled with 5 g of coal.

(3) The container is immersed in a metal bath preheated to 300° C. or 350° C. After the temperature of the metal bath returns to the preheating temperature, heating at a rate of 3° C./min is continued until the rotation of the stirrer stops.

The distance between the lowest horizontal bar and the bottom of the container is 1.6 mm, and the distance between the horizontal bars in the axial direction is 3.2 mm. The two central horizontal bars form an angle of 180 degrees in the rotational direction. The upper and lower horizontal bars also form an angle of 180 degrees in the rotational direction. The two central horizontal bars and the two upper and lower horizontal bars form an angle of 90 degrees in the rotational direction.

A coal or a caking additive is thermally plasticized by heating and has fluidity, and the molten coal or caking additive is re-solidified by further heating. After the Gieseler fluidity is measured, the coal or caking additive heated at a temperature equal to or higher than the re-solidification temperature of the coal or caking additive becomes semicoke 16 in the container 12. The temperature at which the coal or caking additive thermally plasticized by the heating re-solidifies is referred to as a re-solidification temperature. The coal, caking additive, and semicoke 16 are also plastic. After the measurement of the Gieseler fluidity, therefore, the semicoke 16 comes into contact with the inner wall of the container 12 but is pulled by the stirrer 14 and maintains the shape entangled with the stirrer 14. Thus, for most brands of coal or caking additives, as illustrated in FIG. 1, the height, a, of the semicoke 16 adhering to the stirrer 14 from the bottom surface of the container 12 is the highest, and the height, b, of the semicoke 16 in contact with the inner wall of the container 12 from the bottom surface is the lowest. Such behavior of thermoplastic coal or a thermoplastic caking additive is known as the Weissenberg effect.

The heights, a, and, b, can be measured by disassembling the container 12 after measurement. After the measurement of the Gieseler fluidity, the container 12 may be scanned with a microfocus X-ray CT apparatus to capture an image of the shape of the semicoke 16, and the heights, a, and, b, may be measured from the image. The microfocus X-ray CT apparatus is, for example, XTH320LC manufactured by Nikon Corporation or phoenix v|tome|x m300 manufactured by GE Sensing & Inspection Technologies. The heights, a, and, b, vary little in the circumferential direction of the container, and it is therefore only necessary to measure the height in a specific cross section. If there is a difference in height depending on the position in the circumferential direction, the height may be measured in a plurality of cross sections, and the average value of the heights may be used as the height, a, or, b. In the measurement of the Gieseler fluidity, although a coal or a caking additive is heated to its re-solidification temperature or higher, the heights, a, and, b, may be determined before the coal or caking additive is completely re-solidified. For example, the container 12 may be a transparent container, and the shape of a coal or a caking additive may be observed from the outside while the coal or caking additive is heated. The heating may be stopped when no change is observed in the shape of molten coal or a molten caking additive, and the heights, a, and, b, may be determined from the shape.

The shape of the semicoke 16 after the measurement of the Gieseler fluidity depends on the type of coal. It is assumed that a coal or caking additive with a high degree of entanglement or a coal or caking additive with a large height a of the semicoke 16 adhering to the stirrer 14 has excessively high dilatability in its thermoplastic state, easily forms a defect structure in coke after heating, and adversely affects the coke strength. Thus, the inventors considered that the shape of the semicoke 16 in the container is a measure indicating the thermoplasticity having an effect on the strength of coke and examined the relationship between a value indicating the shape of the semicoke 16 and the permeation distance, which is one of the thermoplasticity characteristics of a coal or a caking additive. The value indicating the shape of the semicoke 16 is, for example, the height, a, of the semicoke 16 adhering to the stirrer 14, the height, b, from the bottom surface of the semicoke 16, the difference, a−b, between the height, a, and the height, b, or the degree of entanglement represented by, (a−b)/a. As a result, it was confirmed that there is a correlation between the value indicating the shape of the semicoke 16 after the measurement of the Gieseler fluidity and the permeation distance of a coal or a caking additive.

Thus, there is a correlation between the value indicating the shape of the semicoke 16 after the measurement of the Gieseler fluidity and the permeation distance of a coal or a caking additive. Thus, if a regression equation for the correlation between the value [a, b, a−b, (a−b)/a] indicating the shape of the semicoke 16 after the measurement of the Gieseler fluidity and the permeation distance of a coal or a caking additive is determined by an experiment or the like in advance, an estimated value of the permeation distance of the coal or caking additive can be calculated only by measuring at least one of the values indicating the shape of the semicoke after the measurement of the Gieseler fluidity.

As described above, in the method for evaluating the thermoplasticity of a coal or a caking additive according to the present embodiment, an estimated value of the permeation distance of the coal or caking additive can be calculated from the value [a, b, a−b, (a−b)/a] indicating the shape of the semicoke 16 after the measurement of the Gieseler fluidity. This eliminates the need for special equipment, for example, for heating coal under load to measure the permeation distance. Thus, an estimated value of the permeation distance of coal can be calculated, and the thermoplasticity of a coal or a caking additive can be evaluated using the permeation distance.

A method for measuring Gieseler fluidity is specified as a fluidity test method in JIS M 8801, and similar methods are also specified in ASTM or ISO. Thus, in the measurement according to such a measurement method, even values measured in different experimental facilities or with different experimental apparatuses can be compared. Furthermore, a regression equation for the correlation between the value [a, b, a−b, (a−b)/a] indicating the shape of the semicoke 16 determined in advance and the permeation distance of a coal or a caking additive can be used in another different experimental facility or with another different experimental apparatus.

Although the value indicating the shape of semicoke after measurement by the fluidity test method (Gieseler plastometer method) specified in JIS M 8801 is used in the above description, the disclosed embodiments are not limited thereto. The conditions specified in ASTM D2639 or ISO 10329 are similar to the conditions specified in JIS M 8801, and a method specified in ASTM or the like may also be used. When a Gieseler plastometer is not used, a stirrer with a diameter of 5% to 60% of the inner diameter of a container for a coal or a caking additive is preferably used. Although the stirrer 14 preferably has a horizontal bar, the molten semicoke 16 becomes entangled with the stirrer 14 even without the horizontal bar.

Although an example of determining the permeation distance of a coal or a caking additive using the value indicating the shape of the semicoke 16 after the measurement of the Gieseler fluidity is described in the present embodiment, the disclosure is not intended to be limited to this example. For example, a caking additive or a coal to which a caking additive is added may be used instead of coal to determine the permeation distance of the material. Similar to coal, the material is thermally plasticized by heating by the same mechanism as coal. When the temperature is further increased, the thermoplastic material is re-solidified, and an estimated value of the permeation distance can be calculated from a value indicating the shape of the re-solidified material. Examples of the caking additive include pitches, such as asphalt pitch and coal-tar pitch, bituminous materials, coal-derived extracts and hydrides, and materials that exhibit thermoplasticity upon heating. Thus, the method for evaluating the thermoplasticity of a coal or a caking additive according to the present embodiment can also evaluate the thermoplasticity of a caking additive or a coal to which a caking additive is added.

Furthermore, the apparatus for measuring the shape of semicoke is not limited to the container used in the Gieseler plastometer method. In an apparatus including a container for storing a coal or a caking additive as a sample and a stirrer located in the container, when the sample in the container is heated while the stirrer is rotated, the molten sample may become entangled with the stirrer. The dimensions of the container and the measurement conditions can be appropriately determined. The value indicating the shape of semicoke is measured in this container, and the permeation distance of the same sample is determined by the method described in Patent Literature 1. If a correlation between these measured values is determined in advance, the permeation distance of a coal or a caking additive in any sample can be estimated only by measuring the value indicating the shape of semicoke.

Depending on the brand of coal or caking additive, the semicoke 16 may be entirely pulled by the stirrer 14 and may not be in contact with the inner wall (sidewall) of the container 12 at all. Thus, when a coal or a caking additive has excessively high dilatability or is easily entangled with the stirrer 14, and semicoke is not in contact with the inner wall of the container, the degree of entanglement may be set to 1 by substituting 0 for the height, b. Even in such a case, the degree of entanglement can be calculated to evaluate the thermoplasticity of the coal.

EXAMPLES

Examples are described below. Various coals with different permeation distances were prepared. The value indicating the shape of the semicoke 16 after the measurement of the Gieseler fluidity specified in JIS M 8801 was measured with a microfocus X-ray CT apparatus. More specifically, the relationship between the permeation distance of coal and the height a of semicoke adhering to the stirrer, the height, b, of the semicoke on the inner wall from the bottom surface, the height, a−b, and the degree of entanglement, (a−b)/a, was examined. FIGS. 2 to 5 show the results of the examination. The permeation distance of coal was measured by a method described in Claim 15 of Patent Literature 1.

The method described in Claim 15 of Patent Literature 1 is described below. A sample is prepared by filling a container with a coal or a caking additive. A material with a through-hole in the top and bottom surfaces is put on the sample. The sample is heated while a constant load is applied to the material with a through-hole in the top and bottom surfaces. The permeation distance of a molten sample that has permeated into the through-hole is measured. In a method for evaluating the thermoplasticity of a sample using the measured value, the sample is prepared by pulverizing a coal or a caking additive such that grains with a size of 2 mm or less constitute 100% by mass and filling a container with the pulverized coal or caking additive such that the layer thickness is 10 mm at a bulk density of 0.8 g/cm³. The material with a through-hole in the top and bottom surfaces is placed such that glass beads with a diameter of 2 mm are arranged on the sample at a layer thickness of 80 mm. The sample is heated from room temperature to 550° C. at a heating rate of 3° C./min in an inert gas atmosphere while a load of 50 kPa is applied from the top of the glass beads.

Figure 2:
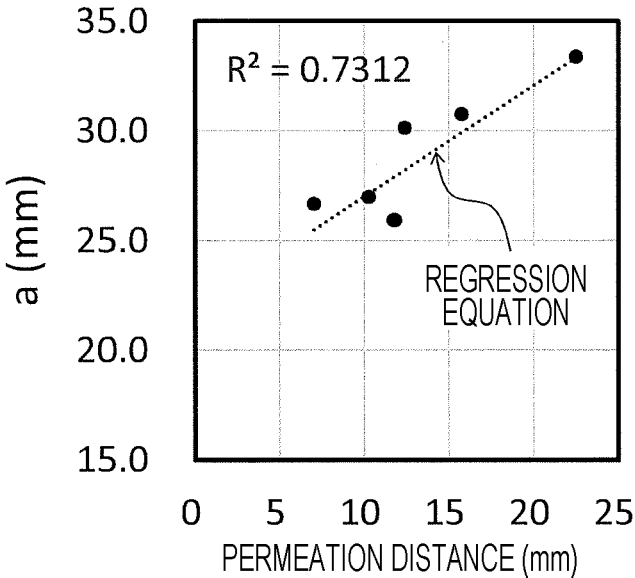
FIG. 2 is a graph of the relationship between the height a of semicoke adhering to a stirrer and the permeation distance of coal.

FIG. 2 is a graph of the relationship between the height a of semicoke adhering to the stirrer and the permeation distance of coal. In FIG. 2, the horizontal axis represents the permeation distance of coal (mm), and the vertical axis represents the height a of semicoke adhering to the stirrer (mm). In FIG. 2, the height, a, increases with the permeation distance of coal, which shows a positive correlation between the permeation distance and the height, a. The coefficient of determination ($R^2$) of the regression equation for the permeation distance and the height, a, was 0.73. This shows that the permeation distance of coal can be estimated using the height, a, of semicoke adhering to the stirrer and the regression equation. The coefficient of determination ($R^2$) is a measure of whether the regression equation fits to actual data.

Figure 3:
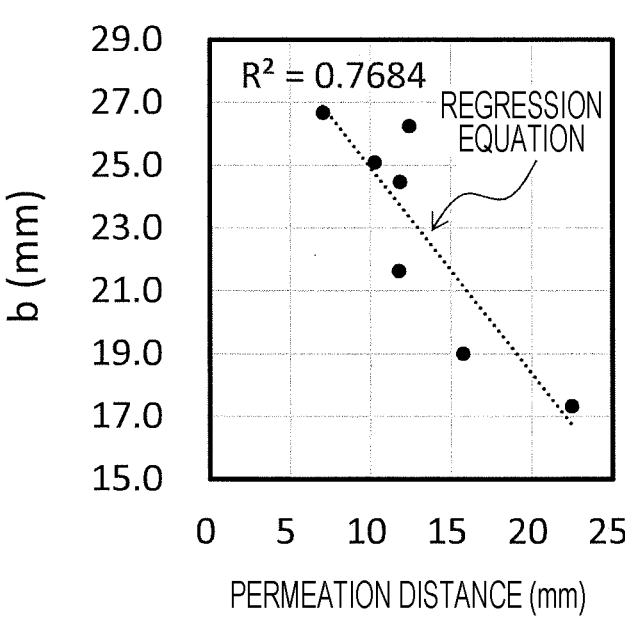
FIG. 3 is a graph of the relationship between the height, b, of semicoke on the inner wall from the bottom surface and the permeation distance of coal.

FIG. 3 is a graph of the relationship between the height, b, of semicoke on the inner wall from the bottom surface and the permeation distance of coal. In FIG. 3, the horizontal axis represents the permeation distance of coal (mm), and the vertical axis represents the height, b, of semicoke on the inner wall from the bottom surface (mm). In FIG. 3, the height, b, decreases as the permeation distance of coal increases, which shows a negative correlation between permeation distance and the height, b. The coefficient of determination ($R^2$) of the regression equation for the permeation distance and the height, b, was 0.77. This shows that the permeation distance of coal can be estimated with high accuracy using the height, b, of semicoke from the bottom surface and the regression equation.

Figure 4:
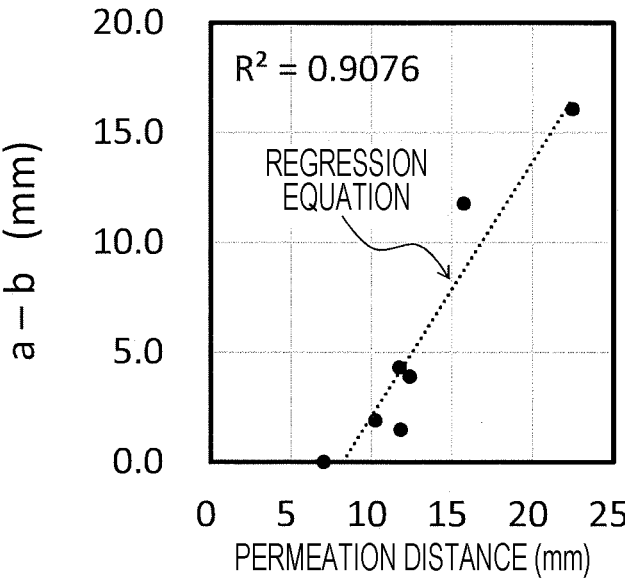
FIG. 4 is a graph of the relationship between the difference, (a–b), between the height, a, of semicoke adhering to a stirrer and the height b of the semicoke from the bottom surface and the permeation distance of coal.

FIG. 4 is a graph of the relationship between the difference, (a−b), between the height, a, of semicoke adhering to the stirrer and the height, b, of the semicoke on the inner wall from the bottom surface and the permeation distance of coal. In FIG. 4, the horizontal axis represents the permeation distance of coal (mm), and the vertical axis represents the height difference, (a−b) (mm). In FIG. 4, the height difference, (a−b), increases with the permeation distance of coal, which shows a positive correlation between the permeation distance and the height difference, (a−b). The coefficient of determination ($R^2$) of the regression equation for the permeation distance and the height difference, (a−b), was 0.91. This shows that the permeation distance of coal can be estimated with high accuracy using the height difference, (a−b), and the regression equation shown in FIG. 4.

Figure 5:
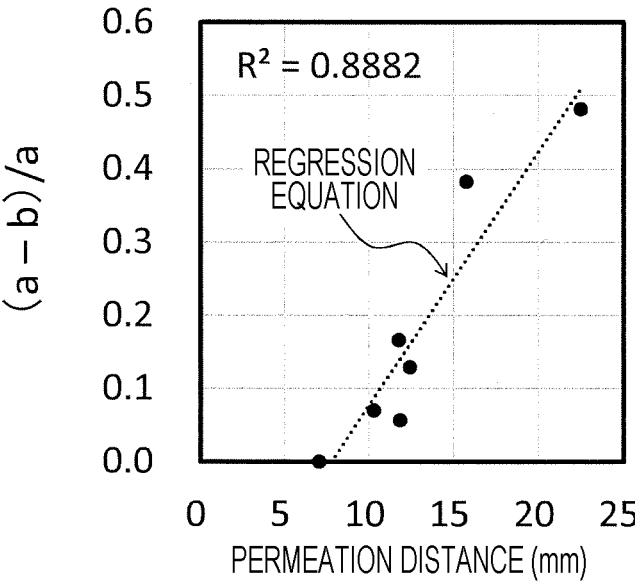
FIG. 5 is a graph of the relationship between the degree of entanglement [(a–b)/a] and the permeation distance of coal.

FIG. 5 is a graph of the relationship between the degree of entanglement [(a−b)/a] and the permeation distance of coal. In FIG. 5, the horizontal axis represents the permeation distance of coal (mm), and the vertical axis represents the degree of entanglement [(a−b)/a]. In FIG. 5, the degree of entanglement [(a−b)/a] increases with the permeation distance of coal, which shows a positive correlation between the permeation distance and the degree of entanglement. The coefficient of determination ($R^2$) of the regression equation for the permeation distance and the degree of entanglement was 0.89. This shows that the permeation distance of coal can be estimated with high accuracy using the degree of entanglement [(a−b)/a] and the regression equation shown in FIG. 5.

Although the examples in FIGS. 2 to 5 are measurement examples in which the permeation distance ranges from 7 to 23 mm under the measurement conditions of Patent Literature 1, a sample with a larger permeation distance can also be examined. However, the height, a, is limited by the size of the container. Thus, to examine a coal or a caking additive with a large permeation distance, the shape of semicoke is preferably measured in a container with a large height or by decreasing the amount of sample. This allows at least a sample with a height, a, of 60 mm or less in a container with a different height in the Gieseler plastometer method or a sample with a permeation distance of 70 mm or less under the measurement conditions of Patent Literature 1 to be examined without problems.

These results show that if the regression equations shown in FIGS. 2 to 5 are determined in advance through an experiment or the like, for coal for which the permeation distance is to be determined, the permeation distance of the coal can be easily calculated only by measuring at least one of the height, a, of semicoke adhering to the stirrer, the height, b, of the semicoke on the inner wall from the bottom surface, the height difference, a−b, and the degree of entanglement, (a−b)/a, which are values indicating the shape of the semicoke after the measurement of the Gieseler fluidity, and by using the measured value and the regression equation, and that the thermoplasticity of the coal can be evaluated using the permeation distance. A person who estimates the permeation distance by determining the value indicating the shape of semicoke (for example, the height, a, of the semicoke adhering to the stirrer, the height, b, of the semicoke on the inner wall from the bottom surface, the height difference, a−b, or the degree of entanglement, (a−b)/a, may be different from a person who determines the correlation (regression equation) between the value indicating the shape of the semicoke and the permeation distance. These persons may also be different from a person who estimates the permeation distance of a coal or a caking additive. In other words, in the method for evaluating the thermoplasticity of a coal or a caking additive according to the present embodiment, it is only necessary to estimate the permeation distance of the coal or caking additive using the value indicating the shape of semicoke and the correlation between the value indicating the shape of semicoke and the permeation distance, and any person can determine the correlation between the value indicating the shape of semicoke and the permeation distance. Although the evaluation of thermoplasticity is described mainly for coal in the present embodiments and examples, the thermoplasticity of the caking additive can also be evaluated in the same manner. More specifically, the targets of the evaluation of thermoplasticity include coals, caking additives, and mixtures of coals and caking additives.

The invention claimed is:

1. A method for evaluating the thermoplasticity of a coal or a caking additive with an apparatus including a container for the coal or the caking additive and a stirrer located in the container, the method comprising:

estimating a permeation distance of the coal or the caking additive from (i) a value indicating a shape of semicoke formed by rotating the stirrer while heating the coal or the caking additive and (ii) a correlation between the value indicating the shape of the semicoke and the permeation distance of the coal or the caking additive.

2. The method for evaluating the thermoplasticity of a coal or a caking additive according to claim 1, wherein the value indicating the shape of the semicoke is at least one of a height b of the semicoke on an inner wall of the container, a height a of the semicoke adhering to the stirrer, a difference a–b between the height a and the height b, and a degree of entanglement (a–b)/a represented by the height a and the height b.

3. The method for evaluating the thermoplasticity of a coal or a caking additive according to claim 1, wherein the apparatus is a Gieseler plastometer, and the coal or the caking additive is heated to a temperature equal to or higher than a re-solidification temperature of the coal or the caking additive.

4. The method for evaluating the thermoplasticity of a coal or a caking additive according to claim 2, wherein the apparatus is a Gieseler plastometer, and the coal or the caking additive is heated to a temperature equal to or higher than a re-solidification temperature of the coal or the caking additive.

* * * * *